United States Patent [19]

Mark

[11] 4,223,170
[45] Sep. 16, 1980

[54] HALOGENATED BISPHENOL-Z AND DERIVATIVES THEREOF

[75] Inventor: Victor Mark, Evansville, Ind.

[73] Assignee: General Electric Company, Pittsfield, Mass.

[21] Appl. No.: 49,630

[22] Filed: Jun. 18, 1979

Related U.S. Application Data

[62] Division of Ser. No. 882,241, Feb. 28, 1978.

[51] Int. Cl.$^2$ ............... C07C 39/17; C07C 39/30; C07C 39/34
[52] U.S. Cl. ............................................. 568/721
[58] Field of Search ................................... 568/721

[56] References Cited

U.S. PATENT DOCUMENTS

| | | | |
|---|---|---|---|
| 1,760,758 | 5/1930 | Korten | 568/721 |
| 2,060,716 | 11/1936 | Avorn | 568/721 |
| 2,883,365 | 4/1959 | Mathes | 568/721 |
| 2,894,004 | 7/1959 | Dretzler | 568/721 |
| 3,029,291 | 4/1962 | Dretzler | 568/721 |
| 3,903,175 | 9/1975 | Meyer | 568/721 |
| 3,960,968 | 6/1976 | Vernaleken et al. | 568/721 |
| 4,075,119 | 2/1978 | Schmidt et al. | 568/721 |

FOREIGN PATENT DOCUMENTS

| | | | |
|---|---|---|---|
| 581636 | 8/1959 | Canada | 568/721 |
| 724240 | 12/1965 | Canada | 568/721 |
| 42-13248 | 7/1967 | Japan | 568/721 |

OTHER PUBLICATIONS

Solmssen, "Chem. Rev.", vol. 37, pp. 481, 556–558 (1945).
Beckoff et al., "J. Am. Oil Chem. Soc.", vol. 32, pp. 64–68 (1955).

Primary Examiner—Norman Morgenstern
Attorney, Agent, or Firm—Salvatore C. Mitri; William F. Mufatti

[57] ABSTRACT

Resistance to high heat distortion is imparted to high molecular weight aromatic polycarbonate resins by controlling the degree to which particular diphenols are halogenated so that there are obtained either highly pure dihalogenated diphenols or predetermined statistical mixtures comprising predominantly mono- and dihalogenated diphenols together with some unreacted diphenol.

3 Claims, No Drawings

HALOGENATED BISPHENOL-Z AND DERIVATIVES THEREOF

This is a division of application Ser. No. 882,241, filed Feb. 28, 1978.

This invention relates to aromatic polycarbonate resins having resistance to high heat distortion.

BACKGROUND OF THE INVENTION

Polycarbonate polymers are known as being excellent molding materials since products made therefrom exhibit such properties as high impact strength, toughness, high transparency, wide temperature limits (high impact resistance below $-60°$ C. and a UL thermal endurance rating of 115° C. with impact), good dimensional stability, good creep resistance, and the like. It would be desirable to add to this list of properties that of resistance to high heat distortion thereby enabling these aromatic polycarbonates to also be used to form molded components that will be exposed to elevated temperature environments such as components exposed to automobile and airplane engines, and the like.

It is known to obtain polycarbonates which contain halogenated monomers as their main, polymeric building blocks. For example, U.S. Pat. No. 3,028,365 discloses a host of polycarbonate compositions including tetrabromobisphenol-A and a dichloromethylenediphenol monomer, as well as processes for obtaining these polycarbonates.

U.S. Pat. No. 3,062,781 discloses that halogenated polycarbonates can be obtained by first halogenating a diphenol containing at least two halogen substituents. However, the only dihalogenated diphenol disclosed is dichlorobisphenol-A.

German Patent P25 20 317.2 discloses that halogenated polycarbonates can be obtained by halogenating bisphenol-A (4,4'-isopropylidenediphenol) to produce a mixture of unreacted bisphenol-A and statistical mixtures of halogenated bisphenol-A (BPA). The halogenated bisphenols disclosed comprise, primarily, tri- and tetrahalogenated BPA.

In general, these prior art references recognize that flame retardance can be imparted to polycarbonates by halogenating the monomeric building blocks from which they are obtained. None of these references, however, discloses or suggests that a high molecular weight polycarbonate resin having resistance to high heat distortion as well as improved flame retardance can be obtained from a particular dihalogenated diphenol.

SUMMARY OF THE INVENTION

It has now been found that resistance to high heat distortion can be imparted to high molecular weight, aromatic polycarbonate resins by selecting appropriate diphenols to be halogenated. In general, this is accomplished by controlling the degree to which the particular diphenols are halogenated. Accordingly, the diphenols are halogenated so that there are obtained either highly pure dihalogenated diphenols or predetermined statistical mixtures comprising predominantly mono- and dihalogenated diphenols together with some unreacted diphenol.

Preferably, these predetermined, statistical, halogenated diphenol mixtures can be continuously obtained by either: (1) dissolving or suspending the diphenol in a solvent system comprising methylene chloride and water and thereafter introducing a halogen into the solvent system; or, (2) dissolving or suspending the diphenol in methylene chloride and then reacting the diphenol with sulfuryl chloride and, optionally, introducing another halogen therein, or, (3) dissolving or suspending the diphenol in methylene chloride and introducing a halogen therein while concurrently purging the reaction with an inert gas. These processes are described in co-pending applications Ser. No. 882,192, filed Feb. 28, 1978, Ser. No. 882,242, filed Feb. 28, 1978, now U.S. Pat. No. 4,210,765, and Ser. No. 882,191, filed Feb. 28, 1978, now abandoned, respectively, all of which are assigned to the same assignee of this case.

While any of the halogens can be employed, chlorine and bromine are preferred and the halogenated diphenols can also include a lower alkyl moiety. Thus, the diphenols that can be used to obtain the high molecular weight aromatic polycarbonates of the invention can be represented by the general formula

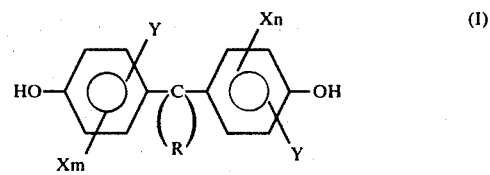

wherein Xm and Xn can each independently be a halogen and mixtures thereof; m and n are each 0.0 to about 2.5 with the proviso that m+n equal at least 0.1 and no more than about 2.5; Y is a $C_1$–$C_4$ alkyl, hydrogen, and mixtures thereof; and, R is a $C_3$–$C_9$ alkylene. In formula I above, the values of m and n represent the number of halogen substituents per mole of monomer.

Typical of some of the diphenols that can be employed in this invention are 4,4'-(cyclohexylidene)diphenol, 4,4'-(cyclopentylidene)diphenol, 4,4'-(cycloheptylidene)diphenol, 4,4'-(cyclooctylidene)diphenol, 4,4'-(cyclohexylidene)di-o-cresol, 4,4'-(cyclopentylidene)di-o-cresol, 4,4'-(cycloheptylidene)di-o-cresol, 4,4'-(cyclooctylidene)di-o-cresol, and the like.

It is possible to employ two or more different diphenols or a copolymer with a glycol or with hydroxy or acid terminated polyester, or with a dibasic acid in the event a carbonate copolymer or interpolymer rather than a homopolymer is desired for use in preparing the aromatic polycarbonate. Blends of any of these materials can also be used to obtain the aromatic polycarbonates.

These halogenated diphenols can then be employed to obtain the high molecular weight aromatic polycarbonates of the invention which can be linear or branched homopolymers or copolymers as well as mixtures thereof or polymeric blends and which generally have an intrinsic viscosity (IV) or about 0.40–1.0 dl/g as measured in methylene chloride at 25° C. These high molecular weight aromatic polycarbonates can be typically prepared by reacting the halogenated diphenol with a carbonate precursor.

The carbonate precursor used can be either a carbonyl halide, a carbonate ester or a haloformate. The carbonyl halides can be carbonyl bromide, carbonyl chloride and mixtures thereof. The carbonate esters can be diphenyl carbonate, di-(halophenyl) carbonates such as di-(chlorophenyl) carbonate, di-(bromophenyl) carbonate, di-(trichlorophenyl) carbonate, di-(tribromophenyl) carbonate, etc., di-(alkylphenyl) carbonate such as di(tolyl) carbonate, etc., di-(naphthyl) carbonate, di-(chloronaphthyl) carbonate, phenyl tolyl carbonate, chlorophenyl chloronaphthyl carbonate, etc., or mixtures thereof. The haloformates that can be used include bis-haloformates of dihydric phenols (bis-chloroformates of hydroquinone, etc.) or glycols (bishaloformates of ethylene glycol, neopentyl glycol, polyethylene glycol, etc.). While other carbonate precursors will occur to those skilled in the art, carbonyl chloride, also known as phosgene, is preferred.

Also included are the polymeric derivatives of a dihydric phenol, a dicarboxylic acid and carbonic acid such as are disclosed in U.S. Pat. No. 3,169,121 which is incorporated herein by reference, and which are particularly preferred. This class of compounds is generally referred to as copolyestercarbonates.

Molecular weight regulators, acid acceptors and catalysts can also be used in obtaining the aromatic polycarbonates of this invention. The useful molecular weight regulators include monohydric phenols such as phenol, chroman-I, paratertiarybutylphenol, para-bromophenol, primary and secondary amines, etc. Preferably, phenol is employed as the molecular weight regulator.

A suitable acid acceptor can be either an organic or an inorganic acid acceptor. A suitable organic acid acceptor is a tertiary amine such as pyridine, triethylamine, dimethylaniline, tributylamine, etc. The inorganic acid acceptor can be either a hydroxide, a carbonate, a bicarbonate, or a phosphate of an alkali or alkaline earth metal.

The catalysts which can be employed are those that typically aid the polymerization of the diphenol with phosgene. Suitable catalysts include tertiary amines such as triethylamine, tripropylamine, N,N-dimethylaniline, quaternary ammonium compounds such as, for example, tetraethylammonium bromide, cetyl triethyl ammonium bromide, tetra-n-heptylammonium iodide, tetra-n-propyl ammonium bromide, tetramethylammonium chloride, tetramethyl ammonium hydroxide, tetra-n-butyl ammonium iodide, benzyltrimethyl ammonium chloride and quaternary phosphonium compounds such as, for example, n-butyltriphenyl phosphonium bromide and methyltriphenyl phosphonium bromide.

Also included herein are branched polycarbonates wherein a polyfunctional aromatic compound is reacted with the diphenol and carbonate precursor to provide a thermoplastic randomly branched polycarbonate. These polyfunctional aromatic compounds contain at least three functional groups which are carboxyl, carboxylic anhydride, haloformyl, or mixtures thereof. Illustrative of polyfunctional aromatic compounds which can be employed include trimellitic anhydride, trimellitic acid, trimellityl trichloride, 4-chloroformyl phthalic anhydride, pyromellitic acid, pyromellitic dianhydride, mellitic acid, mellitic anhydride, trimesic acid, benzophenonetetracarboxylic acid, benzophenonetetracarboxylic anhydride, and the like. The preferred polyfunctional aromatic compounds are trimellitic anhydride and trimellitic acid or their acid halide derivatives.

Blends of linear and branched aromatic polycarbonates are also included within the scope of this invention.

Other well known materials can also be employed for their intended function and include such materials as anti-static agents, mold release agents, thermal stabilizers, ultraviolet light stabilizers, reinforcing fillers such as glass and other inert fillers, foaming agents, and the like.

Accordingly, the high molecular weight aromatic polycarbonates of the invention can be represented by the general formula

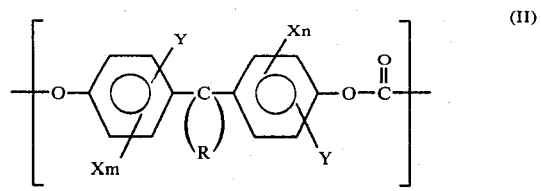

wherein Xm, Xn, m, n, Y and R are the same as identified in formula I above.

PREFERRED EMBODIMENT OF THE INVENTION

The following examples are set forth to more fully and clearly illustrate the present invention and are intended to be, and should be construed as being, exemplary and not limitative of the invention. Unless otherwise stated, all parts and percentages are by weight.

In the following examples, the flame retardancy of the polycarbonates and copolycarbonates obtained was determined by feeding the polycarbonates into an extruder which was operated at about 265° C. and the extrudates were each comminuted into pellets. The pellets were then injection molded at about 315° C. into test bars of about 5 in. by ½ in. by about ⅛-1/8 in. thick. The test bars (5 for each polycarbonate) were then subject to the test procedure set forth in Underwriters' Laboratories, Inc. Bulletin UL-94, Burning Test for Classifying Materials. In accordance with this test procedure, materials so investigated are rated either V-O, V-I or V-II based on the results of 5 specimens. The criteria for each V (for vertical) rating per UL-94 is briefly as follows:

"V-O": Average flaming and/or glowing after removal of the igniting flame shall not exceed 5 seconds and none of the specimens shall drip flaming particles which ignite absorbent cotton.

"V-I": Average flaming and/or glowing after removal of the igniting flame shall not exceed 25 seconds and the glowing does not travel vertically for more than 1/8" of the specimen after flaming ceases and glowing is incapable of igniting absorbent cotton.

"V-II": Average flame and/or glowing after removal of the igniting flame shall not exceed 25 seconds and the specimens drip flaming particles which ignite absorbent cotton.

In addition, a test bar which continues to burn for more than 25 seconds after removal of the igniting flame is classified, not by UL-94, but by the standard of the instant invention, as "burns". Further, UL-94 requires that all test bars in each test group must meet the V type rating to achieve the particular classification. Otherwise, the 5 bars receive the rating of the worst single bar. For example, if one bar is classified as V-II and the other four (4) are classified as V-O, then the rating for all would be V-II.

The moisture barrier properties for the polycarbonates and copolycarbonates in the ensuing examples were determined using Modern Controls, Inc. instruments. Water vapor transmission rate (WVTR) measurements were obtained on an IRD-2C instrument pursuant to ASTM F-372-73 and are based on infrared analysis.

The heat distortion temperature, i.e., heat distortion under load (HDUL), for the polycarbonate and copolycarbonates obtained was determined in accordance with ASTM-D-1637-61. The results are expressed in degrees at a given pressure which, in each instance, was 264 psi.

As is known to those skilled in the art, glass transition temperature (Tg°) can be used in place of HDUL results as HDUL results cannot be greater than Tg° results. Where glass transition temperatures are given, they were determined using a Perkin-Elmer DSC-2B instrument which measures the second order transition temperature by differential scanning calorimetry (DSC).

EXAMPLE 1

Preparation of 2,2'-Dichloro-4,4'-cyclohexylidenediphenol

Into a slurry of 268.3 parts by weight (1.0 partmole) 4,4'-cyclohexylidenediphenol (BPC) in 3000 parts by weight methylene chloride, that was being purged by a slow nitrogen stream, there was introduced, at ambient temperature in the course of ca. 2 hours, 142 parts by weight (2.0 partmole) chlorine gas. In the ensuing, mildly exothermic reaction, the refluxing solvent kept the reaction temperature between 40° and 45° C. After the addition of chlorine was completed, the colorless solution was sampled by gas chromatographic analysis which showed the following composition:

| Compound | Retention Time (Min) | Composition (Mole %) |
|---|---|---|
| 4,4'-cyclohexylidenediphenol | 19.57 | 0.1 |
| 2-chloro-4,4'-cyclohexylidenediphenol | 20.82 | 5.6 |
| 2,2'-dichloro-4,4'-cyclohexylidenediphenol | 23.15 | 92.1 |
| 2,2',6-trichloro-4,4'-cyclohexylidenediphenol | 25.27 | 2.2 |
| Reference (4-cumylphenol) | 12.36 | |

Recrystallization from water-methanol yielded colorless crystals of 2,2'-dichloro-4,4'-cyclohexylidenediphenol (DCBPC), 99.6% pure, melting point 148.5°–149.5° C. Elemental analysis confirmed the structure by matching its correct elemental composition. Chlorine: found, 21.0; theoretical, 21.0%. Carbon: found, 64.0; theoretical, 64.1%. Hydrogen: found, 5.3; theoretical 5.4%.

EXAMPLE 2

Preparation of the Polycarbonate of 2,2'-Dichloro-4,4'-cyclohexylidenediphenol (DCBPC)

Into a mixture of 84.3 parts by weight of the highly pure 2,2'-dichloro-4,4'-cyclohexylidenediphenol (DCBPC) (0.25 partmole), 300 parts by volume water, 300 parts by volume methylene chloride, 0.47 parts by weight phenol, 0.5 part by weight triethylamine, and 50% aqueous NaOH solution to raise the pH to 11.4, there was introduced, at ambient temperature, 30 parts by weight phosgene in 30 minutes while maintaining the pH of the two phase system at approximately 11 (between 10 and 12.5) by simultaneously adding a 25% NaOH solution. At the end of the addition period, the pH of the aqueous phase was 11.7 and the diphenol content was less than 1 part per million (ppm) as determined by ultraviolet analysis. The methylene chloride phase was separated from the aqueous phase, washed with an excess of dilute aqueous hydrochloric acid (0.01 normal), and three times with deionized water. The polymer was precipitated by adding the neutral and salt-free methylene chloride solution to an excess of methanol and filtering off the white polymer which was dried at 95° C. The properties found for the resultant, pure DCBPC polycarbonate are set forth in the Table.

EXAMPLE 3

The procedure of Example 2 was repeated except that a mixture of 75.9 parts by weight (0.225 partmole) 2,2'-dichloro-4,4'-cyclohexylidenediphenol (DCBPC) and 5.7 parts by weight (0.025 partmole) 4,4'-isopropylidenediphenol (BPA) was employed in place of the highly pure 2,2'-dichloro-4,4'-cyclohexylidenediphenol (DCBPC). The properties found for the resultant polycarbonate are set forth in the Table.

EXAMPLE 4

The procedure of Example 2 was repeated except that a mixture of 42.2 parts by weight (0.125 partmole) 2,2'-dichloro-4,4'-cyclohexylidenediphenol and 33.5 parts by weight (0.125 partmole) 4,4'-cyclohexylidenediphenol (BPC) was used in place of the highly pure DCBPC. The properties found for the resultant polycarbonate are set forth in the Table.

EXAMPLE 5

Preparation of 4,4'-Cycloheptylidenediphenol

Into a solution of 112.7 parts by weight (1.0 partmole) cycloheptanone and 470 parts by weight (5.0 partmole) phenol there was introduced gaseous hydrobromic acid. The mildly exothermic reaction was moderated by external cooling, keeping the reaction temperature between 30° and 37° C. after ca. 1.5 hour of reaction time, the red colored mixture thickened and solids began to form. After an additional four hour contact with a slow stream of hydrobromic acid, all acid was removed by placing the stirred mixture under water aspirator vacuum and the solid phase removed by vacuum filtration. Washing the solids with hot water and recrystallizing them by charcoaling from aqueous menthol, yielded white crystals of 4,4'-cycloheptylidenediphenol, melting point 208°–209° C., that were 99.1% pure by gas chromatography analysis (retention time: 25.35 min.; p-cumylphenol reference retention time: 16.47 min.).

EXAMPLE 6

The procedure of Example 2 was repeated except that 70.6 parts by weight 4,4'-cycloheptylidenediphenol was used in place of the DCBPC. The properties found for the resultant polycarbonate are set forth in the Table.

EXAMPLE 7

Preparation of a New Compound: 6,6'-Dichloro-4,4'-cyclohexylidnedi-o-cresol

The procedure of Example 1 was repeated except that 4,4'-cyclohexylidenediphenol was replaced with an equivalent amount of 4,4'-cyclohexylidenedi-o-cresol (296.4 parts by weight; 1.0 partmole), melting point 187°–188° C. Gas chromatography indicated the following composition at the end of the reaction:

| Compound | Retention Time (Min) | Composition (Mole %) |
|---|---|---|
| 4,4'-cyclohexylidenedi-o-cresol | 22.72 | 0.6 |
| 6-chloro-4,4'-cyclohexylidenedi-o-cresol | 24.01 | 3.9 |
| 6,6'-dichloro-4,4'-cyclohexylidenedi-o-cresol | 25.44 | 95.5 |
| Reference (p-cumylphenol) | 14.93 | |

Recrystallization from methanol-water yielded 6,6'-dichloro-4,4'-cyclohexylidenedi-o-cresol in 98.8% purity and a melting point of 136.5°–137.5° C. Elemental analysis confirmed the composition. Carbon: found, 65.5; theoretical 65.8%. Chlorine: found, 19.5; theoretical, 19.4%. Hydrogen: found, 6.1; theoretical, 6.1%.

EXAMPLE 8

The procedure of Example 2 was followed employing a mixture of 45.6 parts by weight 6,6'-dichloro-4,4'-cyclohexylidenedi-o-cresol (0.125 partmole) and 28.5 parts by weight 4,4'-isopropylidenediphenol (BPA) in place of 2,2'-dichloro-4,4'-cyclohexylidenediphenol. The properties found for the resultant copolycarbonate are set forth in the Table.

EXAMPLE 9

The procedure of Example 1 was repeated except that only 71.0 parts by weight (1.0 partmole) chlorine gas instead of 2.0 partmole was employed. The resultant ternary mixture had the following, nearly ideal, statistical composition as indicated by gas chromatographic analysis:

| Diphenol Compound | Retention Time (Min) | Composition (Mole %) |
|---|---|---|
| 4,4'-cyclohexylidenediphenol | 19.61 | 26.2 |
| 2-chloro-4,4'-cyclohexylidenediphenol | 20.85 | 51.2 |
| 2,2'-dichloro-4,4'-cyclohexylidenediphenol | 23.18 | 22.6 |
| Reference (4-cumylphenol) | 12.38 | |

EXAMPLE 10

The procedure of Example 2 was repeated except that the 2,2'-dichloro-4,4'-cyclohexylidenediphenol was replaced with an equivalent amount (75.7 parts by weight) of a statistical mixture consisting of 26.2 mole % BPC, 51.2 mole % 2-chloro-4,4'-cyclohexylidenediphenol and 22.6 mole % DCBPC. The properties found for the resultant polycarbonate are set forth in the Table.

EXAMPLE 11

Preparation of a New Compound: 2,2'-Dibromo-4,4'-Cyclohexylidenediphenol (DBBPC)

To a slurry of 268.3 parts by weight (1.0 partmole) 4,4'-cyclohexylidenediphenol (BPC), 8000 parts by volume methylene choride and 1400 parts by volume water, there was simultaneously added, at ambient temperature and with good stirring, a solution of 168.0 parts by weight sodium bicarbonate in 2500 parts by volume water and 320.0 parts by weight liquid bromine. The addition required ca. one hour during which period the temperature of the slurry rose from 22° C. to 28° C. and all of the solids originally present went into solution forming a light, cream colored, two phase system. After separation from the aqueous phase, gas chromatographic analysis of the methylene phase indicated the following composition:

| Diphenol Compound | Retention Time (Min) | Composition (Mole %) |
|---|---|---|
| 4,4'-cyclohexylidenediphenol | 23.74 | 0.0 |
| 2-bromo-4,4'-cyclohexylidenediphenol | 24.59 | 8.4 |
| 2,2'-dibromo-4,4'-cyclohexylidenediphenol | 26.34 | 83.8 |
| 2,2',6-tribromo-4,4'-cyclohexylidenediphenol | 27.97 | 7.8 |
| Reference (p-cumylphenol) | 16.29 | |

Recrystallization from methylene chloride yielded pure 2,2'-dibromo-4,4'-cyclohexylidenediphenol as white crystals, melting point 165°–167° C., with the correct elemental analysis. Bromine: found, 37.46; theoretical, 37.51%. Carbon: found, 50.62; theoretical 50.73%. Hydrogen: found, 2.80, theoretical, 2.77%.

EXAMPLE 12

The procedure of Example 3 was repeated except that DCBPC was replaced with an equivalent amount of DBBPC (95.9 parts by weight, 0.225 partmole). The properties found for the resultant copolycarbonate are set forth in the Table.

EXAMPLE 13

Preparation of a New Compound: 6,6'-Dibromo-4,4'-Cyclohexylidenedi-o-cresol

The procedure of Example 11 was repeated except that 4,4'-cyclohexylidenediphenol was replaced with an equivalent amount of 4,4'-cyclohexylidenedi-o-cresol (296.4 parts by weight, 1.0 partmole). Work up of the reaction mixture yielded white crystals for which gas chromatography indicated that it contained 96.3 mole % of 6,6'-dibromo-4,4'-cyclohexylidenedi-o-cresol, retention time: 25.57 minutes while the reference, 4-cumylphenol, emerged at 14.88 minutes.

Recrystallization from hexane yielded white crystals with a 99.5% purity and melting point of 137°–138° C. Elemental analysis confirmed the structure. Bromine: found, 34.8; theoretical, 35.2%. Carbon: found, 52.8; theoretical, 52.9%. Hydrogen: found, 4.8; theoretical, 4.9%.

EXAMPLE 14

The procedure of Example 3 was repeated except that the DCBPC was replaced with an equivalent amount of 6,6'-dichloro-4,4'-cyclohexylidenedi-o-cresol (113.5 parts by weight, 0.225 partmole). The properties found for the resultant copolycarbonate are set forth in the Table.

TABLE

Properties of Polycarbonates and Copolycarbonates

| Example No. | I.V. | UL Rating Specimen Thickness | | WVTR | T°g (°C.) | HDUL (°C. @ 264 psi) |
|---|---|---|---|---|---|---|
| | | 1.56 mm | 3.13 mm | | | |
| 2 | 0.560 | V-O | V-O | 0.76 | 181 | 161–163 |
| 3 | 0.566 | V-O | V-O | 2.2 | — | 158 |
| 4 | 0.522 | V-O | V-O | 3.1 | — | 156 |
| 6 | 0.526 | V-II | V-II | 1.3 | 160 | — |
| 8 | 0.538 | V-II | V-O | 4.7 | — | 145 |
| 10 | 0.582 | V-O | V-O | 3.0 | — | 149 |
| 12 | 0.506 | V-O | V-O | 1.67 | — | 159 |

TABLE-continued

| | | Properties of Polycarbonates and Copolycarbonates | | | | |
|---|---|---|---|---|---|---|
| Example No. | I.V. | UL Rating Specimen Thickness 1.56 mm | 3.13 mm | WVTR | T° g (°C.) | HDUL (°C. @ 264 psi) |
| 14 | 0.522 | | | 4.7 | — | 156 |

As can be seen from the results tabulated above, the polycarbonates and copolycarbonates of the invention exhibit excellent resistance to high heat distortion without adversely affecting their other desirable properties. In addition to the results shown in the above Table, the oxygen barrier properties of the polycarbonates and copolycarbonates were also determined using an OX-TRAN 100 instrument, the measurements obtained being based on a coulometric method wherein the results are expressed in cc/24 hrs./100 in$^2$/mil/atmosphere. While all results were acceptable, the oxygen transmission value obtained for the polycarbonate of Example 2 was exceptional at 6.5.

What is claimed is:
1. 6,6'-Dichloro-4,4'-cyclohexylidenedi-o-cresol.
2. 2,2'-Dibromo-4,4'-cyclohexylidenediphenol.
3. 6,6'-Dibromo-4,4'-cyclohexylidenedi-o-cresol.

UNITED STATES PATENT AND TRADEMARK OFFICE
CERTIFICATE OF CORRECTION

PATENT NO. : 4,223,170
DATED : 9/16/80
INVENTOR(S) : Victor Mark

It is certified that error appears in the above–identified patent and that said Letters Patent are hereby corrected as shown below:

Column 6, line 61, typo "-cyclohexyli<u>dnedi</u>" should be
-- -cyclohexyli<u>denedi</u>--

Signed and Sealed this

First Day of September 1981

[SEAL]

Attest:

Attesting Officer

GERALD J. MOSSINGHOFF

Commissioner of Patents and Trademarks